United States Patent
Suzuki

(10) Patent No.: US 6,638,261 B2
(45) Date of Patent: *Oct. 28, 2003

(54) DISPOSABLE PULL-ON DIAPER

(75) Inventor: Seiji Suzuki, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/983,362

(22) Filed: Oct. 24, 2001

(65) Prior Publication Data

US 2002/0049420 A1 Apr. 25, 2002

(30) Foreign Application Priority Data

Oct. 25, 2000 (JP) ........................... 2000-325827

(51) Int. Cl.[7] ........................... A61F 13/15; A61F 13/20
(52) U.S. Cl. ................... 604/385.13; 604/389; 604/391; 604/396
(58) Field of Search ................... 601/386, 389–396, 601/385.13, 385.201, 385.2

(56) References Cited

U.S. PATENT DOCUMENTS

| | | | |
|---|---|---|---|
| 3,776,232 A | * 12/1973 | Schaar | |
| 3,954,106 A | * 5/1976 | Tritsch | |
| 3,995,639 A | * 12/1976 | Cheslow | |
| 4,090,510 A | * 5/1978 | Segersten | |
| 4,209,016 A | * 6/1980 | Schaar | |
| 4,211,226 A | * 7/1980 | Schaar | |
| 4,909,802 A | * 3/1990 | Ahr et al. | |
| 5,358,500 A | * 10/1994 | Lavon et al. | 604/385.29 |
| 5,575,784 A | * 11/1996 | Ames-Ooten et al. | |
| 5,603,794 A | * 2/1997 | Thomas | 604/389 |
| 5,807,371 A | * 9/1998 | Toyoda et al. | 604/385.29 |
| 6,063,066 A | * 5/2000 | Inoue et al. | |
| 6,264,644 B1 | * 7/2001 | Igaue et al. | 604/389 |
| 6,475,205 B2 | * 11/2002 | Shimada et al. | 604/385.13 |
| 2002/0004655 A1 | * 1/2002 | Shimada et al. | 604/385.03 |
| 2002/0026172 A1 | * 2/2002 | Shimada et al. | 604/385.13 |

FOREIGN PATENT DOCUMENTS

| | | |
|---|---|---|
| EP | 0623330 | * 11/1994 |
| EP | 0 890 351 | 1/1999 |
| EP | 1 092 405 | 4/2001 |
| EP | 1 121 917 | 8/2001 |
| EP | 1 121 918 | 8/2001 |
| JP | 9-253123 | 9/1997 |
| JP | 9-253124 | 9/1997 |

OTHER PUBLICATIONS

Derwent Publications Ltd., London, GB; AN 1997–530468 XP002219051 abstract.

* cited by examiner

*Primary Examiner*—Karin Reichle
(74) *Attorney, Agent, or Firm*—Lowe Hauptman Gilman & Berner, LLP

(57) ABSTRACT

A disposable pull-on diaper has a pair of tape fasteners to hold the diaper in a rolled up state. The tape fasteners are provided in the vicinity of transversely opposite side edges of a rear waist region so as to extend in a longitudinal direction. The tape fasteners have lower end portions bonded to the diaper by bonding zones extending in a waist-surrounding direction in the vicinity of peripheral edge portions of respective leg-openings. The bonding zones extend obliquely inward in the waist-surrounding direction from the transversely opposite side edge portions of the rear waist region toward the upper end portions of the respective tape fasteners.

5 Claims, 8 Drawing Sheets

DISPOSABLE PULL-ON DIAPER

BACKGROUND OF THE INVENTION

This invention relates to a disposable pull-on diaper provided with tape fasteners used to fasten the diaper in a rolled up state for disposal.

Japanese Patent Application Publication Nos. 1997-253123A and 1997-253124A describe disposable pull-on diapers of a type comprising a liquid-pervious topsheet, a liquid-impervious backsheet and a liquid-absorbent core disposed between these two sheets so as to configure front and rear waist regions and a crotch region positioned between these waist regions wherein, in the rear waist region, a tape fastener or tape fasteners is (are) attached to the outer surface of the backsheet so that the diaper may be fastened in a rolled up state for disposal after use.

In the diaper described in Japanese Patent Application Publication No. 1997-253123A, a tape fastener is formed by a single tape strip extending in a waist-surrounding direction and having a central portion bonded to the diaper. The remaining right and left side portions of the tape strip are folded up so that these portions may be unfolded rightward and leftward in the waist-surrounding direction. The right and left side portions are provided with bonding zones so as to maintain the folded up state of the diaper.

In the diaper described in Japanese Patent Application Publication No. 1997-253124A, tape fasteners are formed by a pair of strips of adhesive tape extending in parallel to each other in the waist-surrounding direction and spaced apart from each other in the longitudinal direction of the diaper.

For disposal, each of the diapers disclosed in the Publications is rolled from opposite side portions thereof, in a transverse direction, inward and toward the tape fastener(s), and then the tape fastener(s) is/are wound around the diaper and anchored on the outer surface of the backsheet by pressure-sensitive adhesive. The rolled up diaper is fastened by the tape fastener(s) in this manner and remains in the rolled up state.

The diaper disclosed in the Publications requires the user to roll up the diaper from both side portions inward and toward the tape fastener(s), and then wind the tape fastener (s) around the rolled up diaper. Therefor time and labor are required for the operations of rolling up the diaper and winding the tape fastener(s) around this rolled up diaper. In addition, it is impossible to close the waist-opening of the known diaper and there is always anxiety that excretion and/or its odor might leak from the waist-opening.

SUMMARY OF THE INVENTION

It is an object of this invention to provide a disposable pull-on diaper adapted to be easily rolled up and maintained in the rolled up state for disposal after use without any apprehension that excretion and/or its odor might leak from the waist-opening and the pair of leg-openings.

According to this invention, there is provided a disposable pull-on diaper comprising a diaper structure having front and rear waist regions opposed to each other and a crotch region positioned between these waist regions. The front and rear waist regions are connected together in the vicinity of transversely opposite side edge portions thereof to define a waist-opening and a pair of leg-openings. A pair of tape fasteners adapted to fasten the diaper in a rolled up state are attached to the outer surface of the diaper structure and anchoring means or elements are formed on inner surfaces of the tape fasteners facing the outer surface of the diaper structure.

The tape fasteners are provided in the vicinity of the transversely opposite side edge portions in one of the front and rear waist regions so as to extend in a longitudinal direction wherein each of the tape fasteners has an upper end portion lying adjacent the waist-opening and lower end portion lying adjacent the leg-openings. The lower end portions are bonded to the diaper structure by bonding zones extending in a waist-surrounding direction in the vicinity of respective peripheral edges of the leg-openings wherein the bonding zones extend obliquely inward in the waist-surrounding direction from the transversely opposite side edge portions toward the upper end portions.

According to one preferred embodiment of this invention, the lower end portions of the tape fasteners are positioned more inwardly in the waist-surrounding direction than the respective upper end portions of the tape fasteners. Each of the tape fasteners obliquely extends from its lower end portion toward its upper end portion so as to be gradually spaced further away from the other tape fastener.

According to another preferred embodiment of this invention, elastically stretchable members associated with the leg-openings are provided to extend in the leg-surrounding directions. The members are attached under extension to peripheral edge portions of the leg-openings and the bonding zones overlap at least partially the elastically stretchable members associated with the leg-openings.

According to still another preferred embodiment of this invention, the anchoring means or elements are formed by one of pressure-sensitive adhesive agents applied on the tape fasteners and hook members attached to the tape fasteners. Release sheets adapted to temporarily retain the tape fasteners are attached to the outer surface of the diaper structure in the vicinity of the transversely opposite side edge portions.

DETAILED DESCRIPTION OF THE PREFERRED EMBODIMENTS

Details of the disposable pull-on diaper according to this invention will be more fully understood from the description given hereunder with reference to the accompanying drawings.

Figure 1:
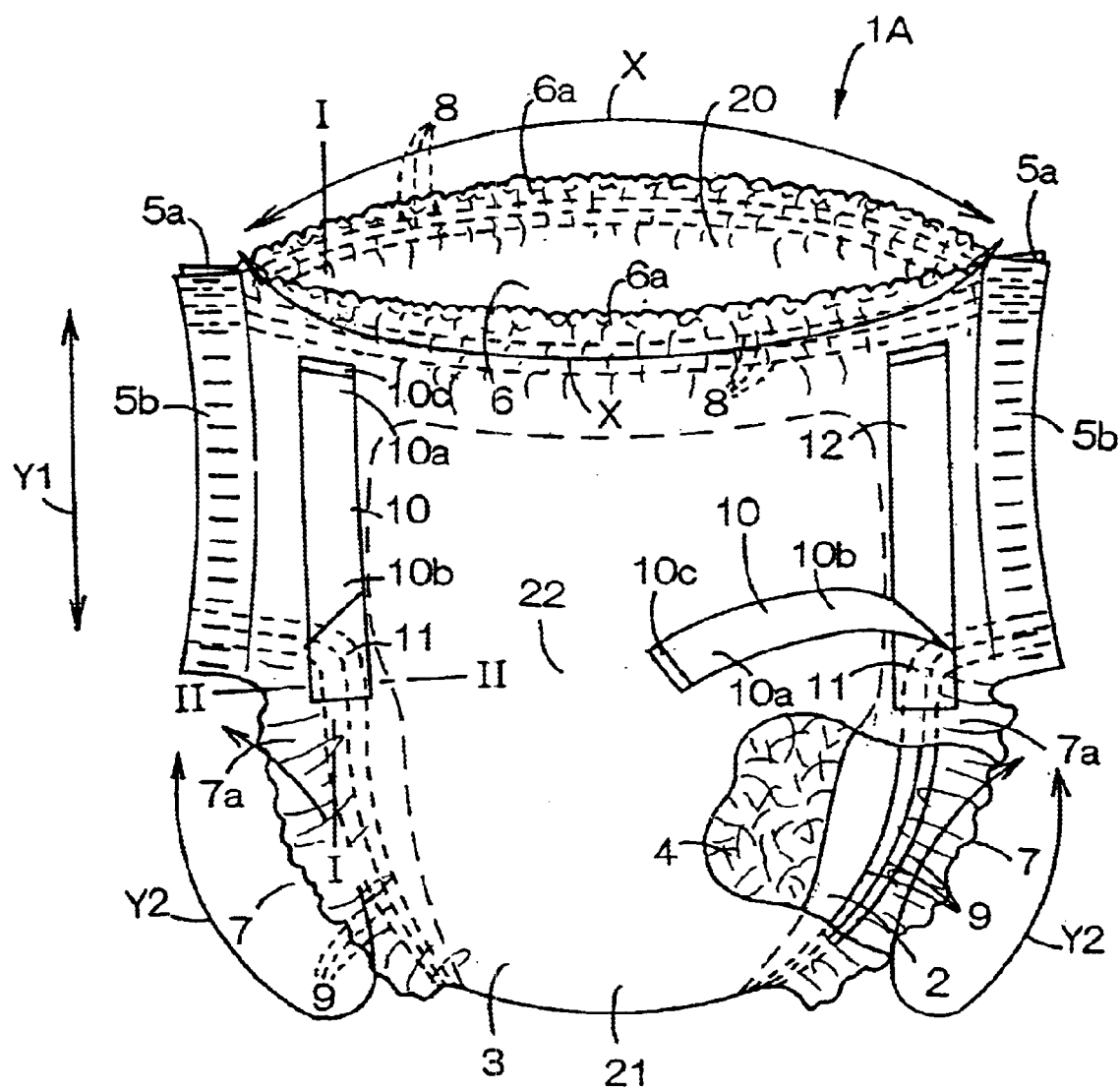
FIG. 1 is a perspective and partially broken away view showing a disposable pull-on diaper according to the invention as viewed from the side of the rear waist region.
Figure 2:
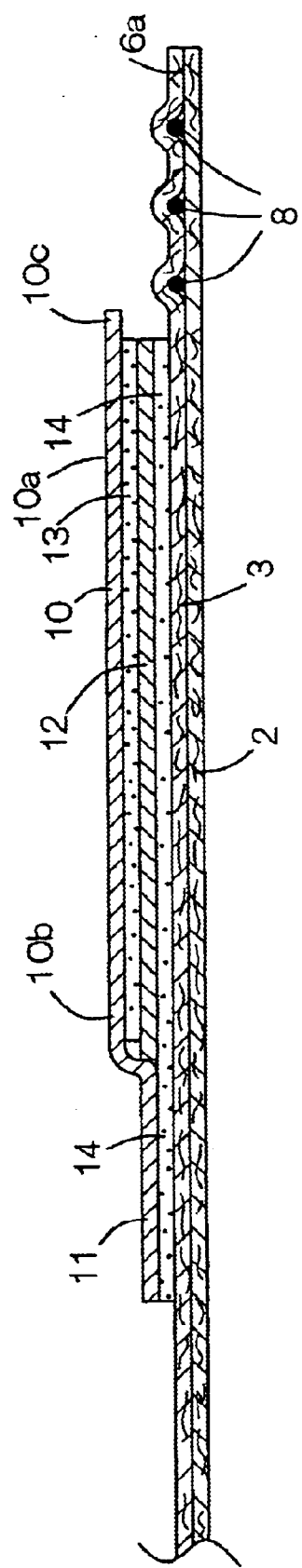
FIG. 2 is a sectional view taken along line I—I in FIG. 1 omitting the elastic elements for clarity.
Figure 3:
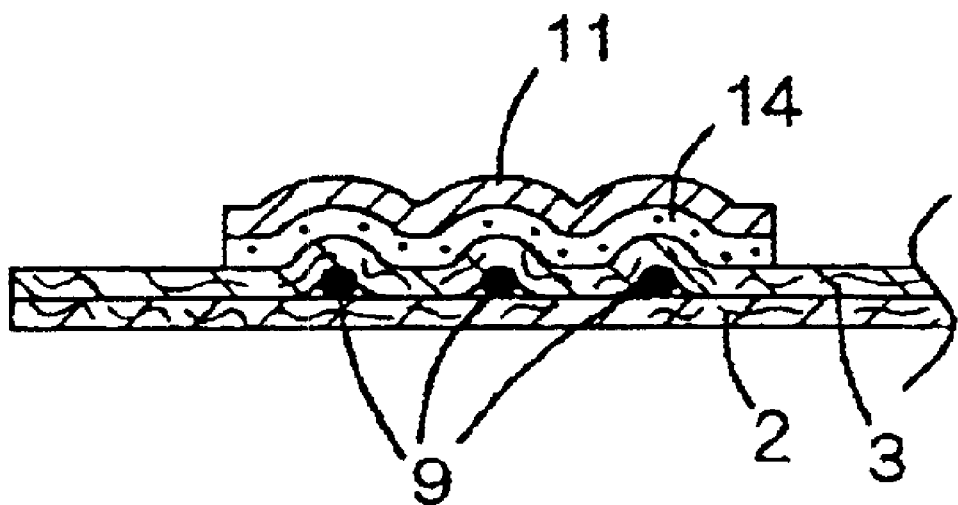
FIG. 3 is a sectional view taken along line II—II in FIG. 1.

In FIG. 1, one of tape fasteners 10 is shown as being separated from a release sheet 12. Referring to FIG. 1, a waist-surrounding direction is indicated by arrow X, a longitudinal direction is indicated by arrow Y1 and leg-surrounding directions are indicated by arrows Y2. Surfaces of topsheet and backsheet 2, 3, the tape fasteners 10, the release sheets 12 and other components which face a core 4 will be referred to herein as "inner surfaces" and opposite surfaces of components 2, 3, 10, 12 which do not face the core 4 will be referred to herein as "outer surfaces".

The diaper 1A shown in FIG. 1 has a diaper structure basically composed of the liquid-pervious topsheet 2, the liquid-impervious backsheet 3 and the liquid-absorbent core 4 disposed between sheets 2, 3 and entirely covered with and bonded to tissue paper (not shown). The core 4 is bonded to the inner surfaces of the topsheet and backsheet 2, 3 with the tissue paper therebetween.

The diaper structure is composed of front and rear waist regions 20, 22 opposed to each other and a crotch region 21 positioned between waist regions 20, 22. The front and rear waist regions 20, 22 are overlaid and bonded together along their transversely opposite side edges 5a, 5b extending in a longitudinal direction so as to define a waist-opening 6 and a pair of leg-openings 7.

Along a peripheral edge portion 6a of the waist-opening 6, an elastic member 8 comprising a plurality of elastic elements expandable in the waist-surrounding direction is disposed between the topsheet and backsheet 2, 3 and bonded under extension to the inner surfaces of sheets 2, 3. Along a peripheral edge portion 7a of each leg-opening 7, an elastic member 9 comprising a plurality of elastic elements expandable in a leg-surrounding direction is disposed between the topsheet and backsheet 2, 3 and bonded under extension to the inner surfaces of the sheets 2, 3. Referring to FIG. 1, a plurality of gathers are formed along the peripheral edge portions 6a, 7a of the waist-opening and leg-openings 6, 7 as the elastic members 8, 9 contract.

In the transversely opposite side edge portions 5b of the rear waist region 22, a pair of tape fasteners 10 are attached to the outer surface of the backsheet 3 so that the used diaper 1A may be fastened by these tape fasteners 10 in a rolled up state. The tape fasteners 10 are made of flexible but non-expandable plastic sheets. The tape fasteners 10 extend in parallel to the transversely opposite side edge portions 5b in the longitudinal direction.

Each of the tape fasteners 10 has an upper end portion 10a lying in the vicinity of the waist-opening 6 and a lower end portion 10b lying in the vicinity of the associated leg-opening 7. Each of the tape fasteners 10 has a lower end portion 10b bonded to the outer surface of the backsheet 3 through a bonding zone 11 extending in the waist-surrounding direction. Each of the tape fasteners 10 is coated on its inner surface with a pressure-sensitive adhesive 13. The upper end portion 10a of each of the tape fasteners 10 is formed with a grip 10c not coated with the pressure-sensitive adhesive 13.

The bonding zones 11 overlap the elastic members 9 associated with the respective leg-openings 7 and extend obliquely inward from the transversely opposite side edge portions 5b of the rear waist region 22 toward the upper end portions 10a in the waist-surrounding direction. In the bonding zones 11, the inner surface of each of the tape fasteners 10 is bonded to the outer surface of the backsheet 3 by adhesive 14. While FIG. 1 shows that the bonding zones 11 completely overlap with the elastic members 9 associated with the leg-openings 7, the desired effect may be achieved by overlapping the bonding zones 11 with at least one of the elastic elements of the elastic members 9 associated with the leg-openings 7.

The release sheets 12 for temporary fixation of the tape fasteners 10 are disposed between the tape fasteners 10 and the backsheet 3. The release sheets 12 are made of flexible plastic sheets having inner surfaces bonded to the outer surface of the backsheet 3 by adhesives 14. Each of the tape fasteners 10 is temporarily fixed to the outer surface of the release sheets 12 by the pressure-sensitive adhesive 13. Hot melt adhesive is preferably used as the adhesives 14. The tape fasteners 10 as well as the release sheets 12 may be firmly bonded to the backsheet 3 using a technique of welding, instead of using adhesive.

Figure 4:
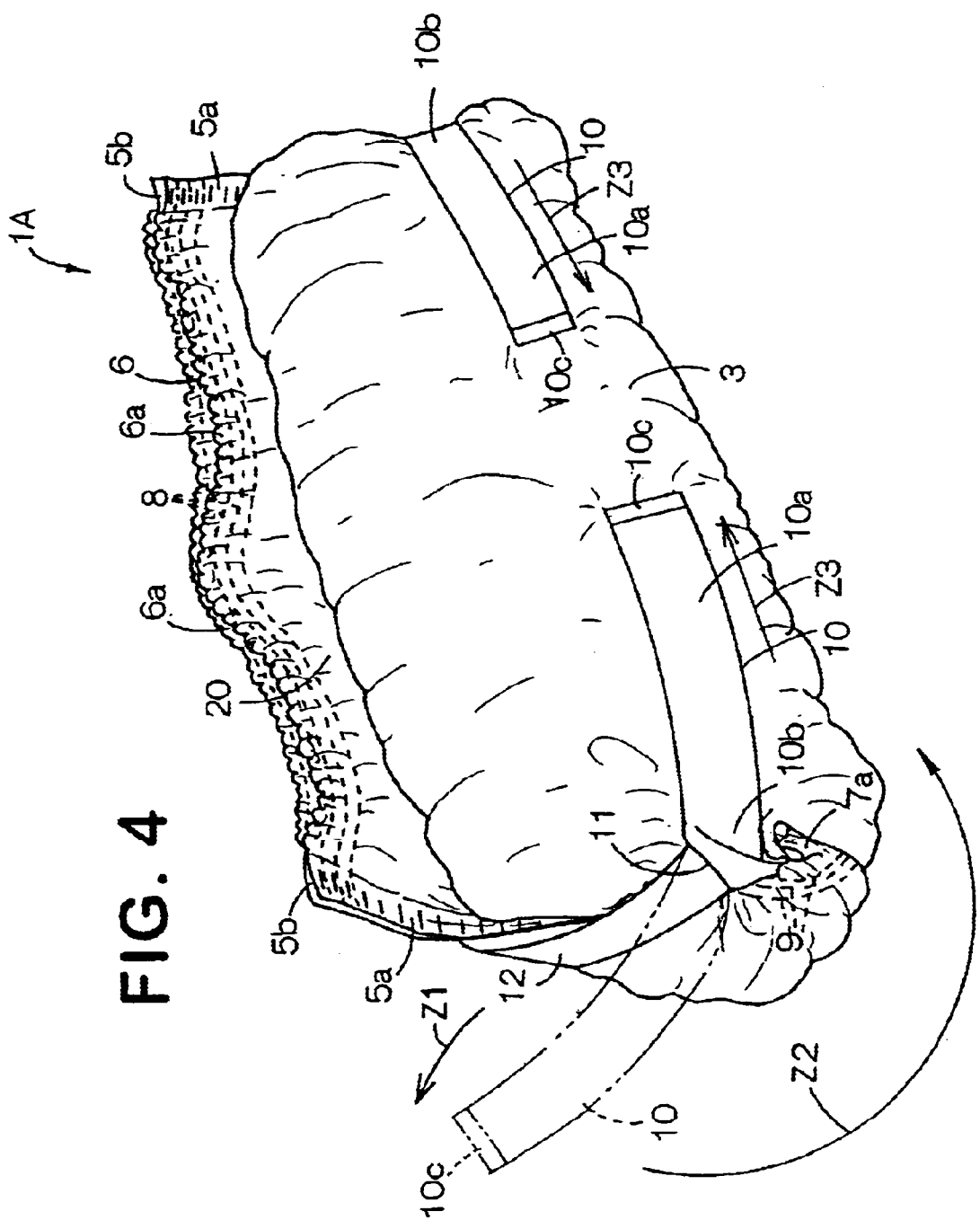
FIG. 4 is a perspective view showing the diaper of FIG. 1 in a rolled up state suitable for disposal.
Figure 5:
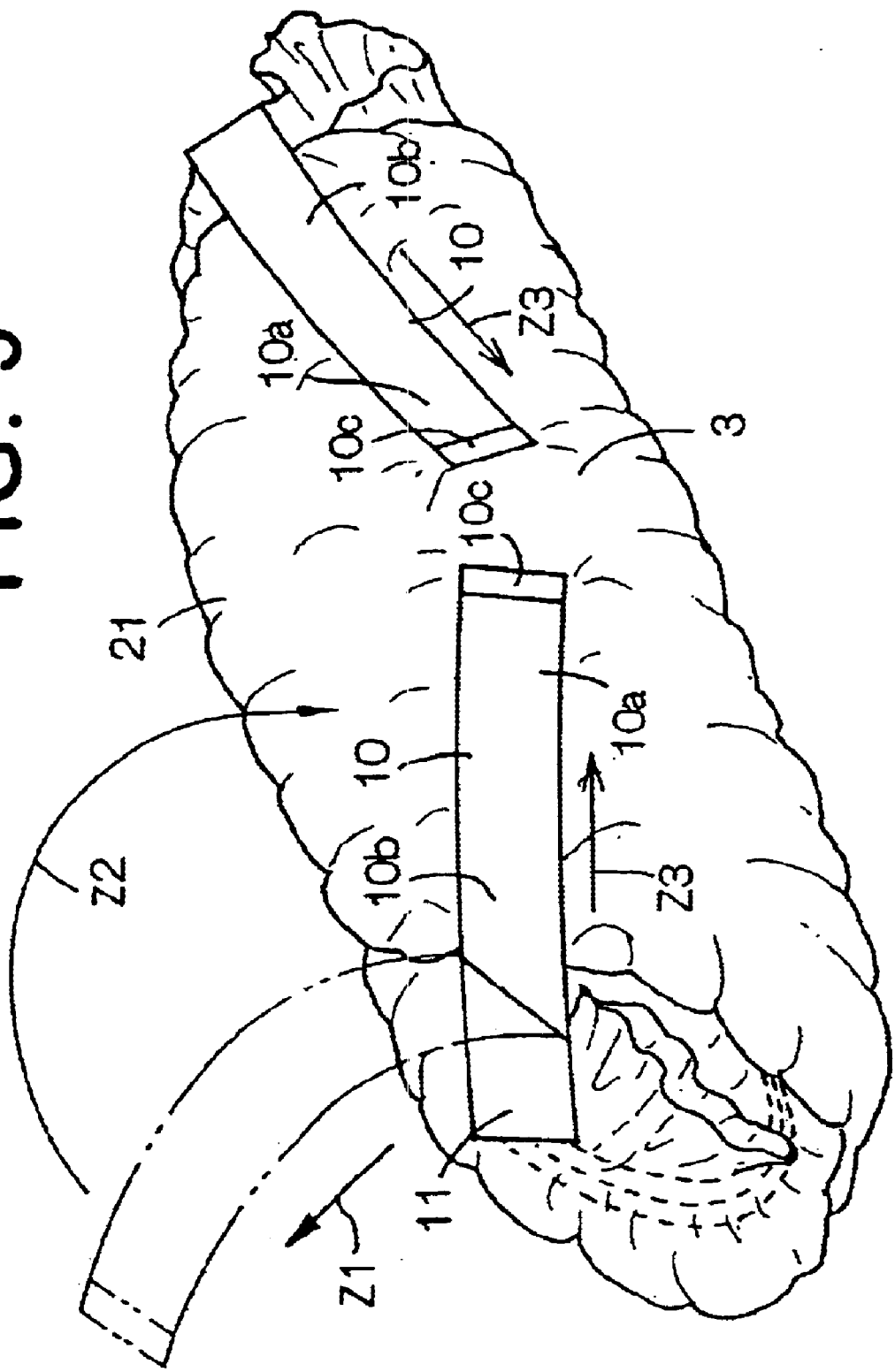
FIG. 5 is a perspective view showing the diaper of FIG. 1 in another rolled up state suitable for disposal.

In FIGS. 4 and 5, phantom lines show one of the tape fasteners 10 in a state after being peeled off the associated release sheet 12 but prior to bonding to backsheet 3 of the rolled diaper. Referring to FIG. 4, the diaper 1A has been rolled up in the longitudinal direction starting from the crotch region 21 toward the peripheral edge portion 6a of the waist-opening 6 with the front waist region 20 inside. Referring to FIG. 5, the diaper 1A has been rolled up in the longitudinal direction starting from the peripheral edge portion 6a of the waist-opening 6 toward the crotch region 21 with the front waist region 20 inside. With the diaper 1A rolled up in either manner, each of the tape fasteners 10 is anchored on the outer surface of the backsheet 3 by means of pressure-sensitive adhesive 13.

To fasten the rolled up diaper 1A with the tape fasteners 10, the tape fasteners 10 are peeled off the respective release sheets 12 by holding the respective grips 10c of the fasteners 10 with fingers. Then, the peeled tape fasteners 10 are pulled around the rolled up diaper in a direction indicated by arrow Z2 and pressed against the outer surface of the backsheet 3.

The bonding zones 11 extend obliquely, so the respective tape fasteners 10 extend obliquely outward as indicated by phantom lines in FIGS. 4 and 5 as the tape fasteners 10 are peeled off in the direction Z1. According to this embodiment, once the tape fasteners 10 have been peeled off the respective release sheets 12, the tape fasteners 10 can be easily anchored to the backsheet 3 of the rolled up diaper 1A merely by guiding the tape fasteners 10 in the direction indicated by arrow Z2, without having to change the directions of the tape fasteners 10, and then pressing the tape fasteners 10 against the outer surface of the backsheet 3.

The bonding zones 11 are overlapped with the respective elastic members 9 associated with the leg-openings 7 so that an elongational force is exerted on the elastic members 9 if the tape fasteners are stretched in a direction indicated by arrow Z3. By pulling the tape fasteners 10 in a direction indicated by arrow Z3 to stretch the elastic members 9 and the peripheral edge portions 7a of the leg-openings 7, and anchoring the tape fasteners 10 on the outer surface of the backsheet 3, when the diaper is in a rolled-up state, the elastic members 9 as well as the peripheral edge portions 7a of the respective leg-openings 7 are held under extension in the direction indicated by arrow Z3, and the leg-openings 7 will be reliably closed by the stretched peripheral edge portions 7a.

According to this embodiment, it is ensured that the rolled diaper 1A is fastened by the tape fasteners 10 and the leg-openings 7 are reliably maintained in the closed state by the peripheral edge portions 7a. Consequently, there is no anxiety that the leg-openings 7 closed in this manner might be unintentionally reopened and excretion and/or its odor might leak from the leg-openings 7. When the diaper 1A has been rolled as seen in FIG. 5, the peripheral edge portion 6a of the waist-opening 6 is confined within the rolled up diaper 1A and therefore there is no anxiety that the waist-opening 6 might be unintentionally exposed to outside and excretion and/or its odor might leak from the waist-opening 6.

Figure 6:
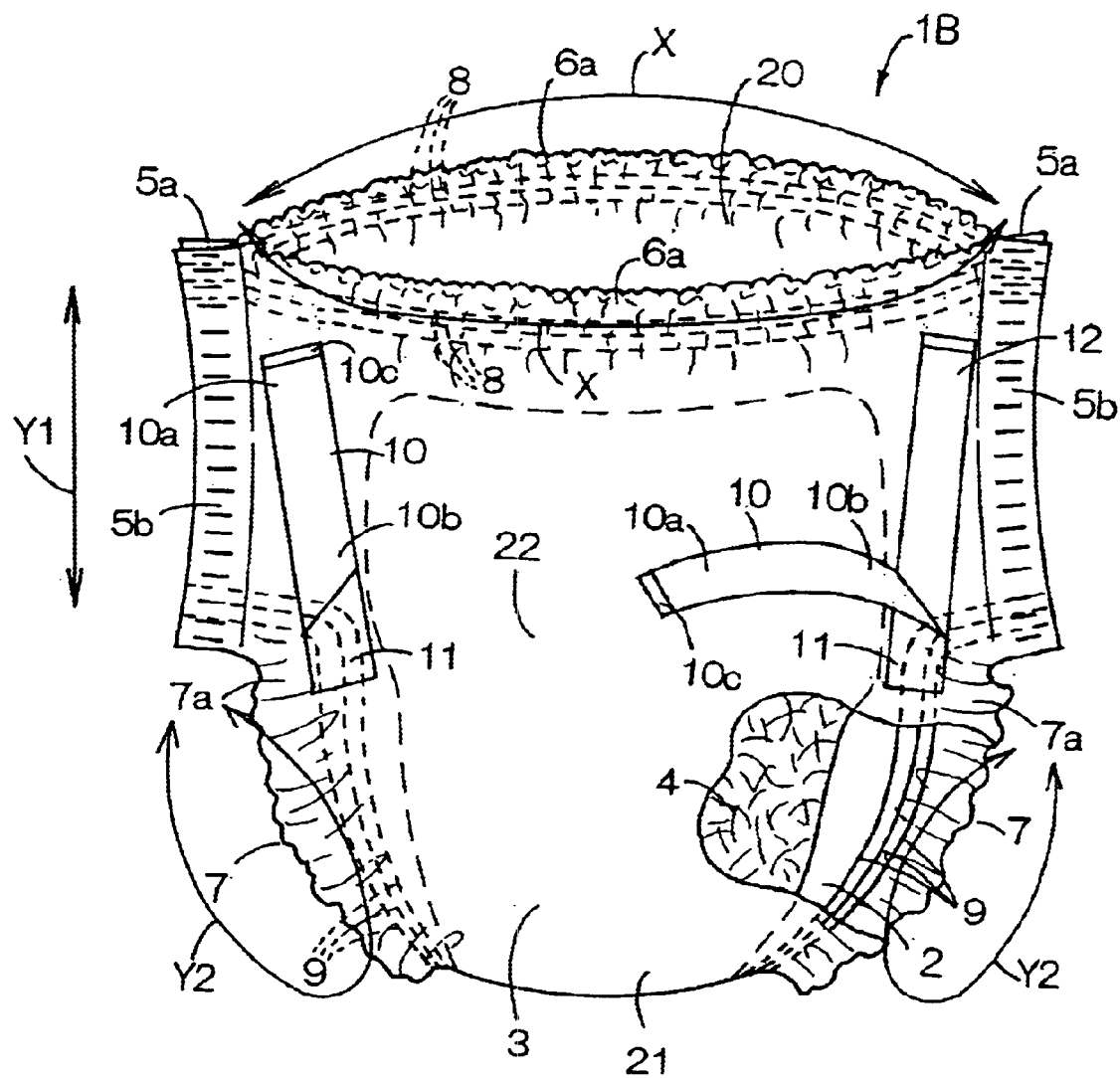
FIG. 6 is a perspective and partially broken away view showing another embodiment of the diaper of the invention.
Figure 7:
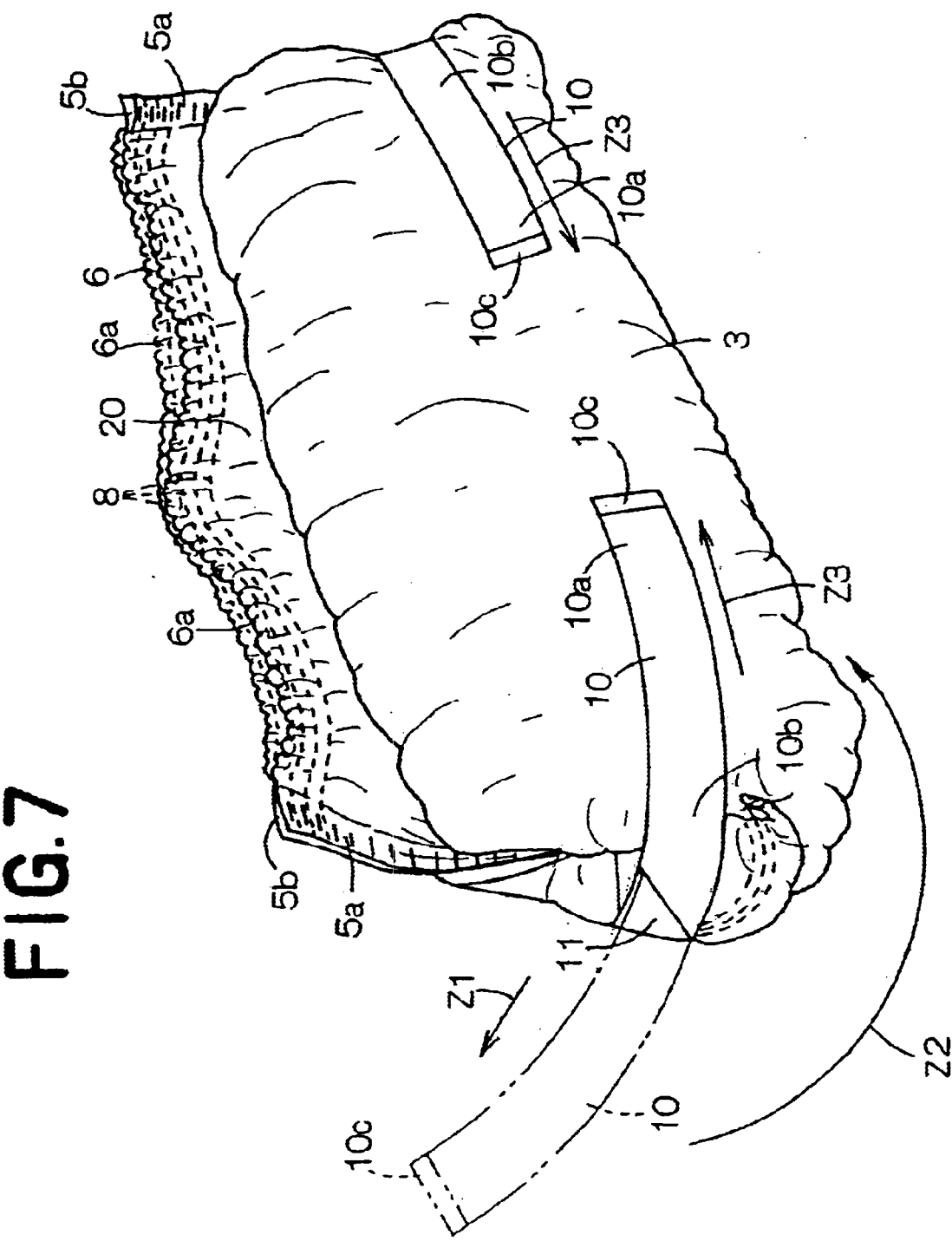
FIG. 7 is a perspective view showing the diaper of FIG. 6 in a rolled up state suitable for disposal.

FIG. 6 illustrates the diaper 1B as viewed from the side of the rear waist region 22 with one of the tape fasteners 10 having been peeled off from the associated release sheet 12. FIG. 7 illustrates the diaper 1B in a rolled-up state with the phantom lines depicting one of the tape fasteners 10 in a state after being peeled off the associated release sheet 12, but prior to being bonded to backsheet 3 of the rolled diaper.

The configuration of the diaper 1B is basically similar to that of the diaper 1A illustrated in FIG. 1 and a detailed description thereof will therefore be eliminated. The diaper 1B of FIG. 6 is different from the diaper 1A of FIG. 1 in that the lower end portion 10b of each of the tape fasteners 10 is positioned more inwardly than the upper end portion 10a in the waist-surrounding direction, and the tape fasteners 10 obliquely extend so that tape fasteners 10 are gradually spaced further away from each other from the lower end portions 10b toward the upper end portions 10a.

As illustrated in FIG. 7, the diaper 1B has been rolled up in the longitudinal direction starting from the crotch region 21 toward the peripheral edge portion 6a of the waist-opening 6 with the front waist region 20 inside. Once the diaper 1B has been rolled up, the tape fasteners 10 are anchored on the outer surface of the backsheet 3 by pressure-sensitive adhesive (not shown).

In the diaper 1B according to this alternative embodiment, the pair of tape fasteners 10 obliquely extend so that tape fasteners 10 are gradually spaced further away from each other from the lower end portions 10b toward the upper end portions 10a, and the bonding zones 11 extend obliquely inward in the waist-surrounding direction from the transversely opposite side edge portions 5b toward the respective upper end portions 10a. Therefore, peeling the tape fasteners 10 off sheets 12 in the direction Z1 causes the tape fasteners 10 to extend laterally as indicated by phantom lines in FIG. 7. Once the tape fasteners 10 have been peeled off, tape fasteners 10 may be merely wound in the direction Z2, without having to redirect the tape fasteners 10, and anchored on the outer surface of the backsheet 3 of the rolled diaper.

The diaper 1B is similar to the diaper 1A of FIG. 1 in that the tape fasteners 10 may be additionally pulled in the direction Z3 to stretch the elastic members 9 associated with the leg-openings 7 and the peripheral edge portions 7a of the leg-openings 7. In this way, the diaper 1B is held by the tape fasteners 10 in a rolled up state while the leg-openings 7 are maintained in a closed state with the peripheral edge portions 7a being stretched in the direction Z3.

It is also possible to roll the diaper 1B starting from the peripheral edge portion 6a of the waist-opening 6 toward the crotch region 21, in the longitudinal direction, with the front waist region 20 inside.

Each tape fastener 10 may be provided, in addition to the non-stretchable plastic sheet, with an elastically stretchable elastomer, such as synthetic or natural rubber, or a composite material of such an elastomer bonded under extension to nonwoven fabric.

Figure 8:
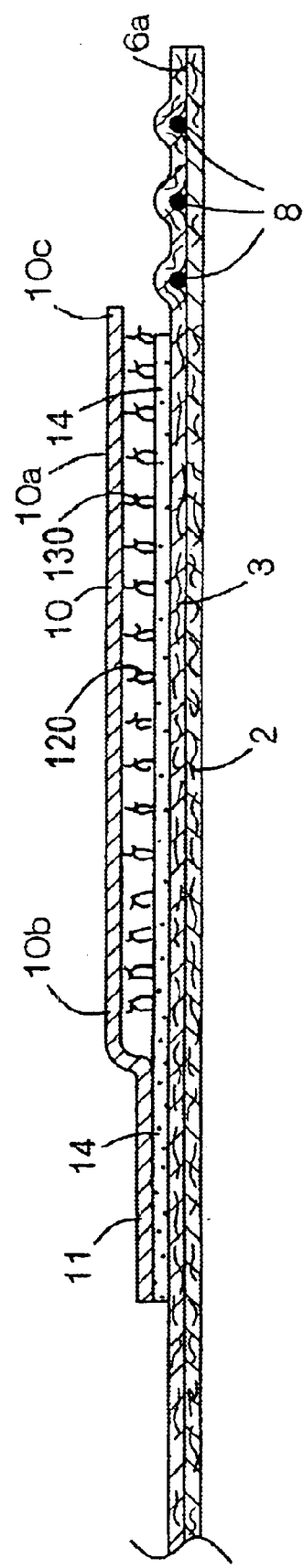
FIG. 8 is a sectional view similar to FIG. 2 showing yet another embodiment of the diaper of the invention.

When the backsheet 3 is made of fibrous nonwoven fabric, it is possible to attach a hook member, such as a hook component of a mechanical fastener, to the inner surface of each of the tape fasteners 10, instead of coating the inner surfaces of the tape fasteners 10 with pressure-sensitive adhesives 13. In this case, the hook member is engaged with component fibers of the fibrous nonwoven fabric so that the tape fasteners 10 may be reliably anchored on the outer surface of the backsheet 3 of the rolled up diapers 1A, 1B. If the hook members (130, FIG. 8) are used, it is possible to replace the release sheets 12 by loop members (120, FIG. 8) which may be attached to the outer surface of the backsheet 3 in the vicinity of transversely opposite side edge portions 5b of the rear waist region 22. It is also possible to attach the tape fasteners 10 as well as the release sheets 12 to the outer surface of the backsheet 3 in the vicinity of the transversely opposite side edges 5a of the front waist region 20.

The topsheet 2 may be formed by a liquid-pervious hydrophilic sheet or nonwoven fabric or a porous plastic film. The backsheet 3 may be formed by hydrophobic nonwoven fabric, a liquid-impervious plastic film or a laminated sheet of hydrophobic nonwoven fabric with a plastic film. It is also possible to make backsheet 3 from nonwoven composite fabric made by a melt blown process and having high water resistance which fabric is sandwiched between two layers of spun bond fibrous nonwoven fabric having high strength and flexibility.

The nonwoven fabric may be selected from a group including spun lace-, needle punch-, melt blown-, thermal bond-, spun bond-, chemical bond-and air through-nonwoven fabric. Component fiber of the nonwoven fabric may be selected from a group including polyolefine-, polyester- and polyamide-based fibers and polyethylene/polypropylene or polyethylene/polyester core-sheath type conjugated fiber and side-by-side-type conjugated fiber.

The core 4 is a mixture of fluff pulp, high absorption polymer grains and thermoplastic synthetic resin fiber compressed to a desired thickness. The high absorption polymer may be selected from a group including starch-based polymer cellulose-based polymer and synthetic polymer.

Bonding of the topsheet and backsheets 2, 3, the core 4 and attachment of the elastic members 8, 9 may be carried out using suitable adhesive such as hot melt adhesive or a technique of welding such as sonic-sealing or heat-sealing.

According to this invention, the diaper may be rolled up, after use, in the longitudinal direction starting from the crotch region toward the waist-opening, or starting from the peripheral edge portion of the waist-opening toward the crotch region. The tape fasteners may be peeled off the respective release sheets, then guided around the rolled up diaper, without changing their directions, and anchored on the outer surface of the backsheet of the rolled up diaper. In this manner, the operations of rolling up the used diaper and anchoring the tape fasteners on the rolled up diaper can be carried out more easily than in the conventional diaper.

The used diaper is reliably held by the tape fasteners in the rolled up state with the leg-openings well maintained in the closed state by the stretched peripheral edge portions thereof. In this way, there is no anxiety that the leg-openings might be unintentionally reopened and excretion and/or its odor might leak from the leg-openings.

When the diaper is rolled up starting from the peripheral edge portion of the waist-opening toward the crotch region in the longitudinal direction, the peripheral edge portion of the waist-opening is confined within the rolled up diaper and therefore there is no anxiety that the waist-opening might be exposed and excretion and/or its odor might leak from the waist-opening.

What is claimed is:

1. A disposable pull-on diaper comprising:
    a diaper structure comprising front and rear waist regions opposed to each other and a crotch region positioned between said waist regions, said front and rear waist regions being permanently connected together in a vicinity of respective transversely opposite side edge portions thereof to define a waist-opening and a pair of leg-openings;

a pair of tape fasteners, adapted to fasten said diaper after use in a rolled up state, being attached to an outer surface of said diaper structure; and means for anchoring said diaper in the rolled up state formed on inner surfaces of said tape fasteners facing the outer surface of said diaper structure;

wherein:

said tape fasteners are provided in the vicinity of said transversely opposite side edge portions, respectively, in one of said front and rear waist regions so as to extend in a longitudinal direction thereof;

said tape fasteners respectively have releasable upper end portions lying adjacent said waist-opening and lower end portions lying adjacent respective said leg-openings, said upper end portions including said anchoring means, said lower end portions being permanently bonded to said diaper structure by bonding zones extending in a circumferential direction of the waist-opening in a vicinity of respective peripheral edges of said leg-openings; and said bonding zones extending obliquely inward in said circumferential direction from said transversely opposite side edge portions in a vicinity of respective said leg openings toward said upper end portions.

2. The disposable pull-on diaper according to claim 1, wherein said lower end portions of respective said tape fasteners are positioned more inwardly in said circumferential direction with respect to said upper end portions of respective said tape fasteners, wherein said tape fasteners extend obliquely from their lower end portions toward their upper end portions so as to be gradually spaced further away from each other.

3. The disposable pull-on diaper according to claim 1, further comprising a plurality of elastically stretchable members which are associated with said leg-openings, extend in circumferential directions of said respective said leg-opening, and are attached under extension to peripheral edge portions of respective said leg-openings; and wherein said bonding zones to at least partially overlap with said elastically stretchable members associated with respective said leg-openings.

4. The disposable pull-on diaper according to claim 1, wherein said anchoring means are formed by pressure-sensitive adhesives; and release sheets, adapted to temporarily retain said pressure-sensitive adhesives of said tape fasteners, are attached to the outer surface of said diaper structure in the vicinity of said transversely opposite side edge portions.

5. The disposable pull-on diaper according to claim 1, wherein said anchoring means comprise hook members;

said diaper further comprising loop members adapted to temporarily retain said hook members of said tape fasteners, said loop members being attached to the outer surface of said diaper structure in the vicinity of said transversely opposite side edge portions.

* * * * *